United States Patent [19]

Charonis et al.

[11] Patent Number: 4,870,160

[45] Date of Patent: Sep. 26, 1989

[54] POLYPEPTIDES WITH LAMININ ACTIVITY

[75] Inventors: Aristidis S. Charonis; Leo T. Furcht, both of Minneapolis, Minn.

[73] Assignee: Regents of the University of Minnesota, Minneapolis, Minn.

[21] Appl. No.: 87,157

[22] Filed: Aug. 19, 1987

[51] Int. Cl.$^4$ .............................................. C07K 7/08
[52] U.S. Cl. .................................................... 530/326
[58] Field of Search ....................... 530/328, 327, 326; 514/15, 14, 13

[56] References Cited

U.S. PATENT DOCUMENTS 4,565,789 1/1986 Liotta et al. .................... 260/112 R

FOREIGN PATENT DOCUMENTS 0021152 7/1981 European Pat. Off. .
0244688 11/1987 European Pat. Off. .

OTHER PUBLICATIONS

Graf et al., Biochemistry 26, pp. 6896–6900 (1987).
Chemical Abstracts, vol. 109, 1988 (Columbus, Ohio, U.S.) Y. Christiane et al: "Laminin and Type III Procollagen, Peptide Inhumarpreovulatory Follicular Fluid", see p. 398 abstract 108013q. e Fertil. Steril. 1988, 50(1), 48–51.
Chemical Abstracts, vol. 109, 1988, (Columbus, Ohio U.S.) R. Okazaki et al.: "Serum Levels of Laminin and Type III Procollagen Peptide in Relation to Diabetic Microangiopathy," see p. 488, abstract 52615t, & Tonyobyo (Tokyo) 1988, 31(1), 7–13.
Chemical Abstracts, vol. 109, 1988, (Columbus, Ohio, U.S.), L. Hartl et al.: "The N Terminus of Laminin A Chain Ishomologous to the B. Chains" see p. 258, abstract 19085x, & Eur. J. Biochem. 1988, 173(3), 629–35.
Chemical Abstracts, vol. 109, 1988, (Columbus, Ohio U.S.) Y. Iwamoto et al.: "Synthetic Derta Peptide from the B1 Chain of Laminin Promotes B16F10 Melanoma Cell Migration", see p. 444, abstract 4628c, & J. Cell. Physiol. 1988, 134(2), 287–91.
Chemical Abstracts vol. 108, 1988 (Columbus, Ohio U.S.) Y. Iwamoto et al., "YI65R Asyhthetic Laminin Pentapeptide, Inhibits Experimental Metastasis Formation", see p. 29 abstract 68408t, Science (Washington, D.C., 1883) 1987, 238 (4830 1132–4.
Chemical Abstracts, vol. 107, 1987 (Columbus, Ohio U.S.) M. Sasaki et al.: "Structure of Adhering Protein, Laminan, and Determination of Adhering Peptide", see p. 292, abstract 19310V Jikken Igaku 1987, 5(7), 650–2.
Chemical Abstracts, vol. 103, 1986 (Columbus Ohio U.S.) P. Liesi et al.: "A Synthetic Peptide of Laminin Specifically Inhibits Neurite Outgrowth of Central Neuronson Laminin" see p. 454, abstract 22265d, Synth Pept. Biol. Med., Proc. Labsystems Res. Symp. 1985, 209–11.
Chemical Abstracts, vol. 99, 1983, (Columbus, Ohio U.S.) cc. Howe et al. "Structural Analysis of Three Subunits of Laminin from Teratocarcinoma-Derived Parietal Endoderm Cells", see p. 249 No. 66173j.
Charonis et al., *J. Cell Biol.* 100: 1848–1853 (1985).
Charonis et al., *J. Cell. Biol.*, 103: 1689–1697 (1986).
Edgar et al., *EMBO J.*, 3 1463–1468 (1986).
Engel et al., *J. Mol Biol.* 150: 97–120 (1981).
Furcht et al., *Bio. Mol. Gen of Cancer Met.* (1985).
Horwitz et al., *J. Cell. Biol.* 101: 2134–2166 (1985).

(List continued on next page.)

*Primary Examiner*—Delbert R. Phillips
*Assistant Examiner*—Christina Chan
*Attorney, Agent, or Firm*—Merchant, Gould, Smith, Edell, Welter & Schmidt

[57] ABSTRACT

A composition which can bind heparin and promote cellular adhesion is provided which consists essentially of a polypeptide of the formula:

arg-tyr-val-leu-pro-arg-pro-val-cys-phe-glu-lys-gly-met-asn-tyr-thr-val-arg, or
glu-leu-thr-asn-arg-thr-his-lys-phe-leu-glu-lys-ala-lys-ala-leu-lys-ile or mixtures thereof.

medical devices such as prosthetic implants, percutaneous devices and cell culture substrates coated with the polypeptide composition are also provided.

3 Claims, 12 Drawing Sheets

OTHER PUBLICATIONS

Kennedy et al., *J. Cell. Physiol.*, 114: 257–262 (1983).
Kyte and Doolittle, *J. Mol. Biol.* 157 105–132 (1982).
Laurie, et al., *J. Mol. Biol.* 189: 205–216 (1986).
LeSot et al., *EMBO J.* 2: 861–865 (1983).
Liotta, *Am. J. Path.*, 117: 339–348 (1984).
Malinoff and Wicha, *J. Cell. Biol.*, 96: 1475–1479.
McCarthy et al., *Cancer Met. Rev.*, 4: 125–152 (1985).
Ott et al., *Eur. J. Biochem.*, 123: 63–72 (1982).
Roberts et al., *Proc. Natl. Acad. Sci. U.S.A.*, 82: 1306–1310 (1985).
Sasaki et al., *Proc. Natl. Acad. Sci. U.S.A.*, 84: 935–939 (1987).
Terranova et al., *Proc. Natl. Acad. Sci. U.S.A.* 80: 444–448 (1983).
Timpl et al., *Intl. Rev. Exp. Path.* 29: 1–112 (1986).
Timpl et al., *J. Biol Chem.*, 254: 9933–9937 (1979).
Yurchenco et al., *J. Biol. Chem.*, 260: 7636–7644 (1985).
E. C. Tsilibary and A. S. Charonis, *J. Cell Biol.* 103 (1986), 388(a).

domain I: 1410-1765
domain A: 1377-1409
domain II: 1158-1376
domain III: 751-1157
domain IV: 520-750
domain V: 249-519
domain VI: 1-248

LAMININ BETA 1-CHAIN         FIG. 2

```
           10         20         30         40         50         60         70
    QEPEFSYGCA EGSCYPATGD LLIGRAQKLS VTSTCGLHKP EPYCIVSHLQ EDKKCFICDS RDPYHETLNP 80         90        100        110        120        130        140
    DSHLIENVVT TFAPNRLKIW WQSENGVENV TIQLALEAEF HFTHLIMTFK TFRPAAMLIE RSSDFGKTWG 150        160        170        180        190        200        210
    VYRYFAYDCE SSFPGISTGP MKKVDDIICD SRYSDIEPST EGEVIFRALD PAFKIEDPYS PRIQNLLKIT 220        230        240        250        260        270        280
    NLRIKFVKLH TLGDNLLDSR MEIREKYYYA VYDMVVRGNC FCYGHASECA PVDGVNEEVE GMVHGHCMCR 290        300        310        320        330        340        350
    HNTKGLNCEL CMDFYHDLPW RPAEGRNSNA CKKCNCNEHS SSCHFDMAVF LATGNVSGGV CDNCQHNTMG 360        370        380        390        400        410        420
    RNCEQCKPFY FQHPERDIRD PNLCEPCTCD PAGSENGGIC DGYTDFSVGL IAGQCRCKLH VEGERCDVCK 430        440        450        460        470        480        490
    EGFYDLSAED PYGCKSCACN PLGTTPGGNP CDSETGYCYC KRLVTGQRCD QCLPQHWGLS NDLDGCRPCD 500        510        520        530        540        550        560
    CDLGGALNNS CSEDSGQCSC LPHMIGRQCN EVESGYYFTT LDHYIYEAEE ANLGPGVVVV ERQYIQDRIP 570        580        590        600        610        620        630
    SWTGPGFVRV PEGAYLEFFI DNIPYSMEYE ILIRYEPQLP DHWEKAVITV QRPGKIPASS RCGNTVPDDD 640        650        660        670        680        690        700
    NQVVSLSPGS RYVVLPRPVC FEKGMNYTVR LELPQYTASG SDVESPYTFI DSLVLMPYCK SLDIFTVGGS 710        720        730        740        750        760        770
    GDGEVTNSAW ETFQRYRCLE NSRSVVKTPM TDVCRNIIFS ISALIHQTGL ACECDPQGSL SSVCDPNGGQ 780        790        800        810        820        830        840
    CQCRPNVVGR TCNRCAPGTF GFGPNGCKPC DCHLQGSASA FCDAITGQCH CFQGIYARQC DRCLPGYWGF 850        860        870        880        890        900        910
    PSCQPCQCNG HALDCDTVTG ECLSCQDYTT GHNCERCLAG YYGDPIIGSG DHCRPCPCPD GPDSGRQFAR 920        930        940        950        960        970        980
    SCYQDPVTLQ LACVCDPGYI GSRCDDCASG FFGNPSQFGG SCQPCQCHHN IDTTDPEACD KDTGRCLKCL 990       1000       1010       1020       1030       1040       1050
    YHTEGDHCQL CQYGYYGDAL RQDCRKCVCN YLGTVKEHCN GSDCHCDKAT GQCSCLPNVI GQNCDRCAPN 1060       1070       1080       1090       1100       1110       1120
    TWQLASGTGC GPCNCNAAHS FGPSCNEFTG QCQCMPGFGG RTCSECQELF WGDPDVECRA CDCDPRGIET 1130       1140       1150       1160       1170       1180       1190
    PQCDQSTGQC VCVEGVEGPR CDKCTRGYSG VFPDCTPCHQ CFALWDAIIG ELTNRTHKFL EKAKALKISG 1200       1210       1220       1230       1240       1250       1260
    VIGPYRETVD SVEKKVNEIK DILAQSPAAE PLKNIGILFE EAEKLTKDVT EKMAQVEVKL TDTASQSNST
```

FIG. 2 (Cont.)

```
         1270       1280       1290       1300       1310       1320       1330
   AGELGALQAG AESLDKTVKE LAEQLEFIKN SDIQGALDSI TKYFQMSLEA EKRVNASTTD PNSTVEQSAL 1340       1350       1360       1370       1380       1390       1400
   TRDRVEDLML ERESPFKEQQ EEQARLLDEL AGKLQSLDLS AAAQMTCGTP PGADCSESEC GGPNCRTDEG 1410       1420       1430       1440       1450       1460       1470
   EKKCGGPGCG GLVTVAHSAW QKAMDFDRDV LSALAEVEQL SKMVSEAKVR ADEAKQNAQD VLLKTNATKE 1480       1490       1500       1510       1520       1530       1540
   KVDKSNEDLR NLIKQIRNFL TEDSADLDSI EAVANEVLKS GNASTPQQLQ NLTEDIRERV ETLSQVEVIL 1550       1560       1570       1580       1590       1600       1610
   QQSAADIARA ELLLEEAKRA SKSATDVKVT ADMVKEALEE AEKAQVAAEK AIKQADEDIQ GTQNLLTSIE 1620       1630       1640       1650       1660       1670       1680
   SETAASEETL TNASQRISKL ERNVEELKRK AAQNSGEAEY IEKVVYSVKQ NADDVKKTLD GELDEKYKKV 1690       1700       1710       1720       1730       1740       1750
   ESLIAQKTEE SADARRKAEL LQNEAKTLLA QANSKLQLLE DLERKYEDNQ KYLEDKAQEL VRLEGEVRSL

1760
   LKDISEKVAV YSTCL
```

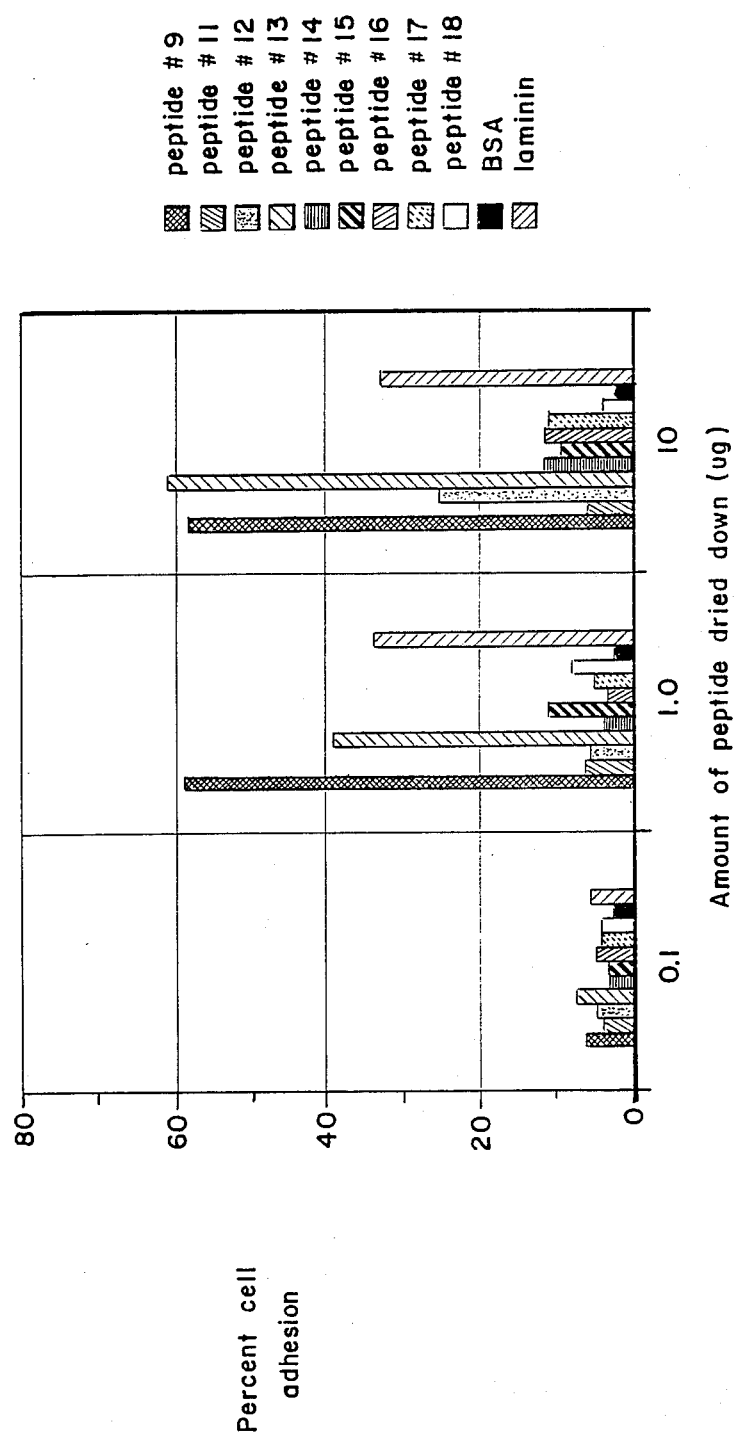

POLYPEPTIDES WITH LAMININ ACTIVITY

This invention was made with Government support under contract number CA 29995 by the U.S. The Government has certain rights in the invention.

BACKGROUND OF THE INVENTION

The adhesion of mammalian cells to the extracellular matrix is of fundamental importance in regulating growth, adhesion, motility and the development of proper cellular phenotype. This has implications for normal development, wound healing, chronic inflammatory diseases, and tumor metastasis. Evidence accumulated over the last several years suggests that the molecular basis for the adhesion of both normal and transformed cells is complex and probably involves several distinct cell surface molecules. Extracellular matrices consist of three types of macromolecules: collagens, proteoglycans and noncollagenous glycoproteins.

One noncollagenous adhesive glycoprotein of interest is laminin. Laminin is a high molecular weight (~850,000) extracellular matrix glycoprotein found almost exclusively in basement membranes. (Timpl et al., *J. of Biol. Chem.*, 254: 9933-9937 (1979)) The basement membrane is an ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another.

Laminin consists of three different polypeptide chains: B1 with 215,000 MW, B2 with 205,000 MW and A with 400,000 MW (Timpl and Dziadek, *Intern. Rev. Exp. Path.*, 29: 1-112 (1986)) When examined at the electron microscopic level with the technique of rotary shadowing, it appears as an asymmetric cross, with three short arms 37 nm long, each having two globular domains, and one long arm 77 nm long, exhibiting a large terminal globular domain (Engel et al., *J. Mol. Biol.*, 150: 97-120 (1981)). The three chains are associated via disulfide and other bonds. Structural data shows that laminin is a very complex and multidomain protein with unique functions present in specific domains.

Laminin is a major component of basement membranes and is involved in many functions. Laminin has the ability to bind to other basement membrane macromolecules and therefore contributes to the structural characteristics of basement membranes. Laminin has been shown to bind to type IV collagen (Charonis et al., *J. Cell. Biol.*, 100: 1848-1853 (1985); Laurie et al., *J. Mol. Biol.*, 189: 205-216 (1986)) exhibiting at least two binding domains (Charonis et al., i J. Cell. Biol., 103: 1689-1697 (1986) Terranova et al., *Proc. Natl. Acad. Sci. U.S.A.*, 80: 444-448 (1983). Laminin also binds to entactin/nidogen (Timpl and Dziadek, supra and to basement membrane-derived heparin sulfate proteoglycan (Laurie et al., *J. Mol. Biol.*, 189: 205-216 (1986). Laminin also has the ability to selfassociate and form oligomers and polymers. Yurchenco et al., *J. Biol. Chem.*, 260: 7636-7644 (1985). Another important functional aspect of laminin is its ability to associate with cell surface molecular receptors and consequently modify cellular phenotype in various ways. A receptor for laminin with a molecular weight of about 68,000 has been observed in various cell types (Lesot et al., *EMBO. J.*, 2: 861-865 (1983; Malinoff and Wicha, J. Cell. Biol., 96: 1475-1479 (1983). However, at least one other and maybe more cell surface receptors for laminin may exist. [See Timpl and Dziadek, supra; Horwitz et al., *J. Cell. Biol.*, 101: 2134-2166 (1985)]. These might include sulfatides, gangliosides [Roberts et al., *Proc. Natl. Acad. Sci. U.S.A.*, 82: 1306-1310 (1985)] or various proteins and proteoglycans. These cell surface molecules may be mediators for the various effects that laminin has on cells. It is known that laminin can directly promote cell adhesion and cell migration of various cell types ranging from normal and malignant mesenchymal cells such as fibroblast and endothelial cells, to various epithelial cells Timpl and Dziadek, supra. However, the exact domains of laminin involved in such processes are not well established yet. For example, it is known that a heparin binding site exists on the A-chain, in the globule of the long arm of laminin (Ott et al., *Eur. J. Biochem.*, 123: 63-72 (1982). However, the exact amino acid sequence of the A-chain is not known and therefore the related oligopeptide can not be identified yet.

Recently, a laminin fragment having a binding domain for a cell receptor without having a binding domain for type IV collagen has been described. U.S. Pat. No. 4,565,789 to Liotta et al. The Liotta patent discloses laminin fragments obtained by digestion of laminin with pepsin or cathepsin G. More specifically, digestion of laminin with pepsin or cathepsin G produces P1 ($M_r$ 280,000) and C1 ($M_r$ 350,000) fragments, wherein the long arm of the molecule is removed and also the globular end regions of the short arms are altered. C1 and P1 fragments having similar molecular weights and binding capacities can also be obtained by digestion of laminin with plasmin and chymotrypsin. Laminin is also known to stimulate neurite outgrowth, a function that has been primarily assigned to the lower part of the long arm of laminin (Edgar et al., *EMBO J.*, 3: 1463-1468 (1986).

The functions that have been described above make laminin an important component of many diverse and clinically important processes such as cell migration, wound healing, nerve regeneration, tumor cell metastasis through vascular walls [Liotta, *Am. J. Path.*, 117: 339-348 (1984); McCarthy et al., Cancer Met. Rev., 4: 125-152 (1985)], diabetic microangiopathy, and vascular hypertrophy due to hypertension. Laminin could also be used in various devices and materials used in humans. In order to better understand the pathophysiology of these processes at the molecular level, it is important to try to assign each of the biological activities that laminin exhibits to a specific subdomain or oligopeptide of laminin. If this can be achieved, potentially important pharmaceuticals based on small peptides producing specific functions of the native, intact molecule, can be synthesized. In order to do this, the exact amino acid sequence of the three laminin chains needs to be determined. Up to now, only the B1 chain has been published. Sasaki, *Proc. Natl. Acad. Sci. U.S.A.*, 84: 935-939 (1987).

Therefore, a need exists to isolate and characterize the subset of peptides within the B1 chain which are responsible for the wide range of biological activities associated with laminin. Such lower molecular weight oligopeptides would be expected to be more readily obtainable and to exhibit a narrower profile of biological activity than laminin itself or the B1 chain thereof, thus increasing their potential usefulness as therapeutic or diagnostic agents.

BRIEF DESCRIPTION OF THE INVENTION

The present invention provides polypeptides which represent fragments of the B1 chain of laminin. The polypeptides can be prepared by conventional solid phase peptide synthesis. The formulas of the two preferred polypeptides are:

arg-tyr-val-val-leu-pro-arg-pro-val-cys-phe-glu-lys-gly-met-asn-tyr-thr-val-arg (F9)

and glu-leu-thr-asn-arg-thr-his-lys-phe-leu-glu-lys-ala-lys-ala-leu-lys-ile. (F13)

Polypeptide F9 formally represents isolated laminin residues 641–660, while polypeptide F13 formally represents isolated laminin residues 1171–1188. The single letter amino acid codes for these polypeptides are RYVVLPRPVCFEKGMNYTVR and ELTNRTHKFLEKAKALKI.

These synthetic polypeptides were assayed for bioactivity and found to be potent promoters of heparin binding to synthetic substrates and of cell adhesion including adhesion of (a) endothelial cells, (b) melanoma cells and (c) fibrosarcoma cells, (d) glioma cells and (e) pheochromocytoma cells. Therefore, it is believed that these polypeptides may be useful to (a) assist in nerve regeneration, (b) promote wound healing and implant acceptance, (c) promote cellular attachment to culture substrata and (d) inhibit the metastasis of malignant cells. Due to the difference in the spectra of biological activities exhibited by polypeptides F9 and F13, mixtures of these peptides is within the scope of the invention.

Furthermore, since it is expected that further digestion/hydrolysis of polypeptides F9 and F13 in vitro or in vivo will yield fragments of substantially equivalent bioactivity, such lower molecular weight polypeptides are considered to be within the scope of the present invention.

BRIEF DESCRIPTION OF THE DRAWINGS

FIG. 2 depicts the primary amino acid sequence of the B1 chain of laminin.

FIGS. 9–13 are graphs depicting cell adhesion to polypeptide fragments of the invention for aortic endothelial cells, M4 melanoma, MM fibrosarcoma, and C6 glioma, and PC12 pheochromocytoma cell lines, respectively.

DETAILED DESCRIPTION OF THE INVENTION

Structure of Laminin and the B1 Chain

Figure 1:
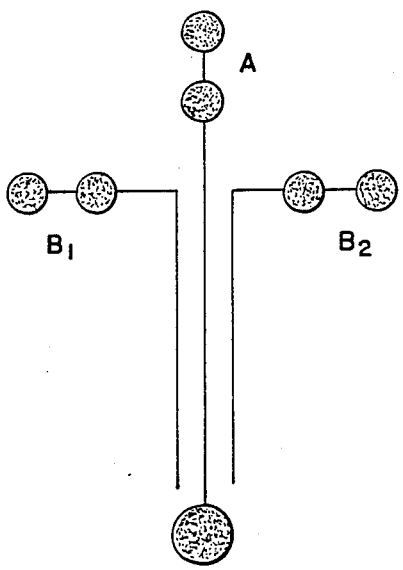
FIG. 1 is a diagrammatic depiction of laminin, indicating the relative location of the A, B1 and B2 chains including globular regions located on each chain.
Figure 3:
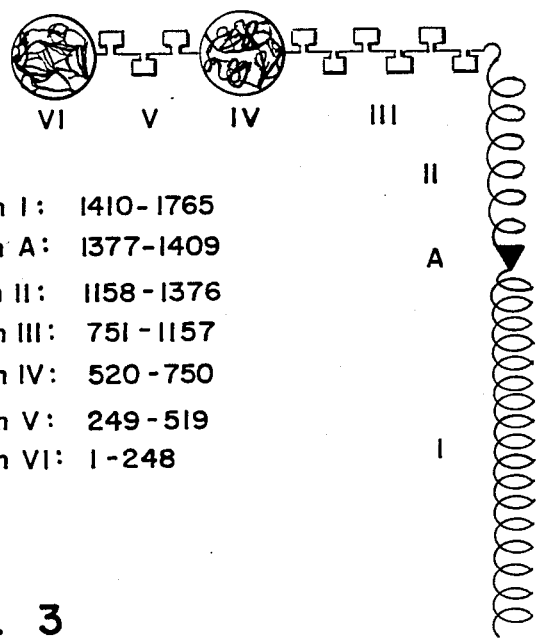
FIG. 3 depicts the organization of domains on the laminin B1 chain.

Referring to FIG. 1, when examined by electron microscope utilizing rotary shadowing techniques, the structure of laminin appears as an asymmetric cross. The three short arms each have two globular domains and are 37 nm in length. The long arm exhibits one large terminal globular domain and is 77 nm in length. Engel et al., supra. As seen in FIG. 1 the three chains are associated via disulfide bonds and other bonds. Of the three polypeptide chains only the B1 chain having a molecular weight of 215,000 has been published. Sasaki et al., supra. The complete sequence of the B1 chain is shown in FIG. 2. In FIG. 3, a schematic of the domain structure of the B1 chain is shown, according to Sasaki et al., supra.

Binding sites for heparin are of special interest since heparin-like macromolecules such as heparan sulfate proteoglycans are present in basement membranes and cell surfaces and therefore their association with laminin may affect basement membrane structure and diverse cellular functions. As indicated previously, it is known that a heparin binding site exists on the A-chain, in the globule of the long arm of laminin (Ott et al, supra); the exact amino acid sequence is not known and therefore no related oligopeptide have been identified. According to the present invention, we have investigated domains of the B1 chain of laminin and synthesized a number of peptide fragments with cell-attachment promoting activity. The polypeptides synthesized and their properties are set forth in Tables 1 and 2, respectively. Peptides F9 and F13 are preferred embodiments of the present invention.

TABLE 1

| F9: RYVVLPRPVCFEKGMNYTVR | 20-mer aa #641–660 |
|---|---|
| F10: WETFQRYRCLENSRSVVK | 18-mer aa #710–727 |
| F11: NIDTTDPEACDKDTGRCLK | 19-mer aa #960–978 |
| F12: VEGVEGPRCDKCTRGY | 16-mer aa #1133–1148 |
| F13: ELTNRTHKFLEKAKALKI | 18-mer aa #1171–1188 |
| F14: VDSVEKKVNEIKDI | 14-mer aa #1199–1212 |
| F15: LERESPFKEQQEEQARL | 17-mer aa #1340–1356 |
| F16: AQKTEESADARRKAEL | 16-mer aa #1685–1700 |
| F17: LERKYEDNQKYLEDKA | 16-mer aa #1722–1737 |
| F18: VCDPGYIGSR | 10-mer aa #924–933 |

| I Isoleucine | V Valine | L Leucine | P Phenylalanine |
|---|---|---|---|
| C Cysteine | M Methionine | A Alanine | G Glycine |
| T Threonine | W Tryptophan | S Serine | Y Tyrosine |
| P Proline | H Histidine | Q Glutamine | N Asparagine |
| K Lysine | R Arginine | E Glutamic acid | D Aspartic acid |

TABLE 2

| PEPTIDE | DOMAIN OF ORIGIN | HYDROPATHY INDEX* | # OF ARGININES AND LYSINES |
|---|---|---|---|
| F9 | IV | −3.9 | 4 |
| F11 | III | −20.7 | 3 |
| F12 | III | −14.8 | 3 |
| F13 | II | −12.9 | 5 |
| F14 | II | −8.4 | 3 |
| F15 | II | −31.1 | 3 |
| F16 | I | −24.8 | 4 |
| F17 | I | −33.9 | 4 |
| F18 | III | −1.3 | 1 |

*Hydropathy index values determined in accord with methodology of J. Kyte and R. F. Doolittle, J. Mol. Biol., 157: 105–132 (1982)

*Synthesis of Polypeptides.* The polypeptides of the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, IL (2d ed.; 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples. In the examples the prefix "F" before each polypeptide referenced in Tables 1 and 2 has been dropped.

EXAMPLE 1. Heparin Binding Assay

Figure 4:
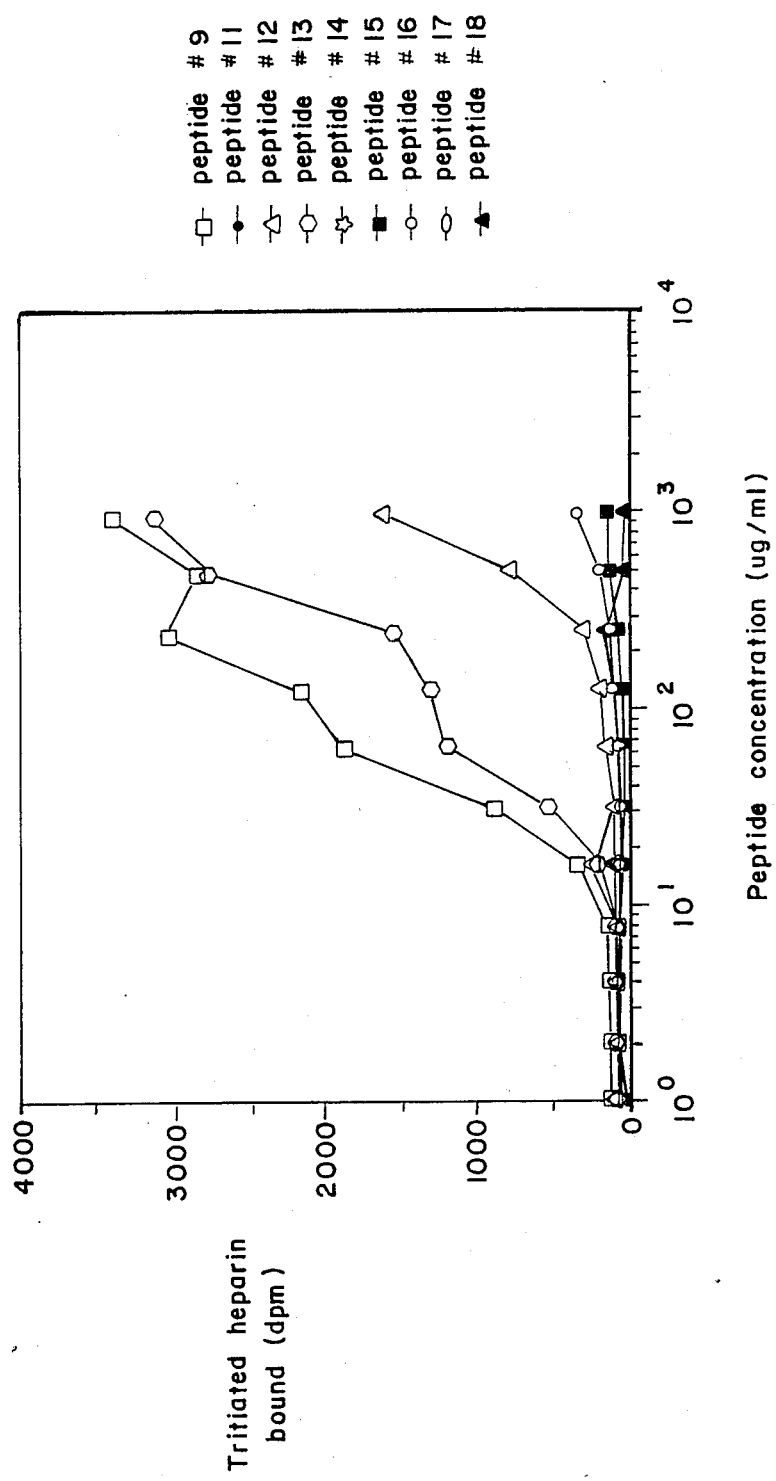
FIG. 4 is a graph depicting the heparin binding activity of polypeptide fragments of the invention.

The assay for heparin binding utilizes nitrocellulose sheets as subtrata to bind peptides or proteins to be tested for heparin binding activity. Peptides 9 and 11-18 were solubilized in 50 mM $NH_3HCO_3$ to form solutions of 1 mg/ml. Each solution was serially diluted 1:1 in the same buffer producing concentrations from 1 mg/ml to 1 $\mu$g/ml. Nitrocellulose sheets which had been pre-soaked in 50 mM $NH_3HCO_3$ were placed in a 96 well dot blot apparatus (Bethesda Research Laboratories, Bethesda, MD, and 100 $\mu$l of various concentrations of each peptide were aspirated through the wells. Each well was then washed three times with binding buffer (10 mM Tris-HCl, pH 8.0, 0.15 M NaCl), and the filters were removed and allowed to air dry overnight. The filters were then equilibrated for 5 minutes at room temperature in binding buffer which contained 10 mM $CaCl_2$. $^3$H-heparin was then diluted to a concentration of 50,000 cpm/ml in binding buffer (with $Ca^{++}$), and nitrocellulose sheets were incubated in the presence of this mixture for 2 hours. The filters were then washed four times with binding buffer, and air dried. The individual spots of samples were cut out of the nitrocellulose, immersed in scintillation fluid and bound heparin was quantitated with a Beckman LS-3801 liquid scintillation counter. The results show that peptides 9 and 13 strongly bound $^3$H-heparin (FIG. 4). While several other peptides bound to $^3$H-heparin the strength of adherance was less than that observed for peptide fragments 9 and 13.

EXAMPLE 2. Peptide Binding to Plastic Plates

Figure 5:
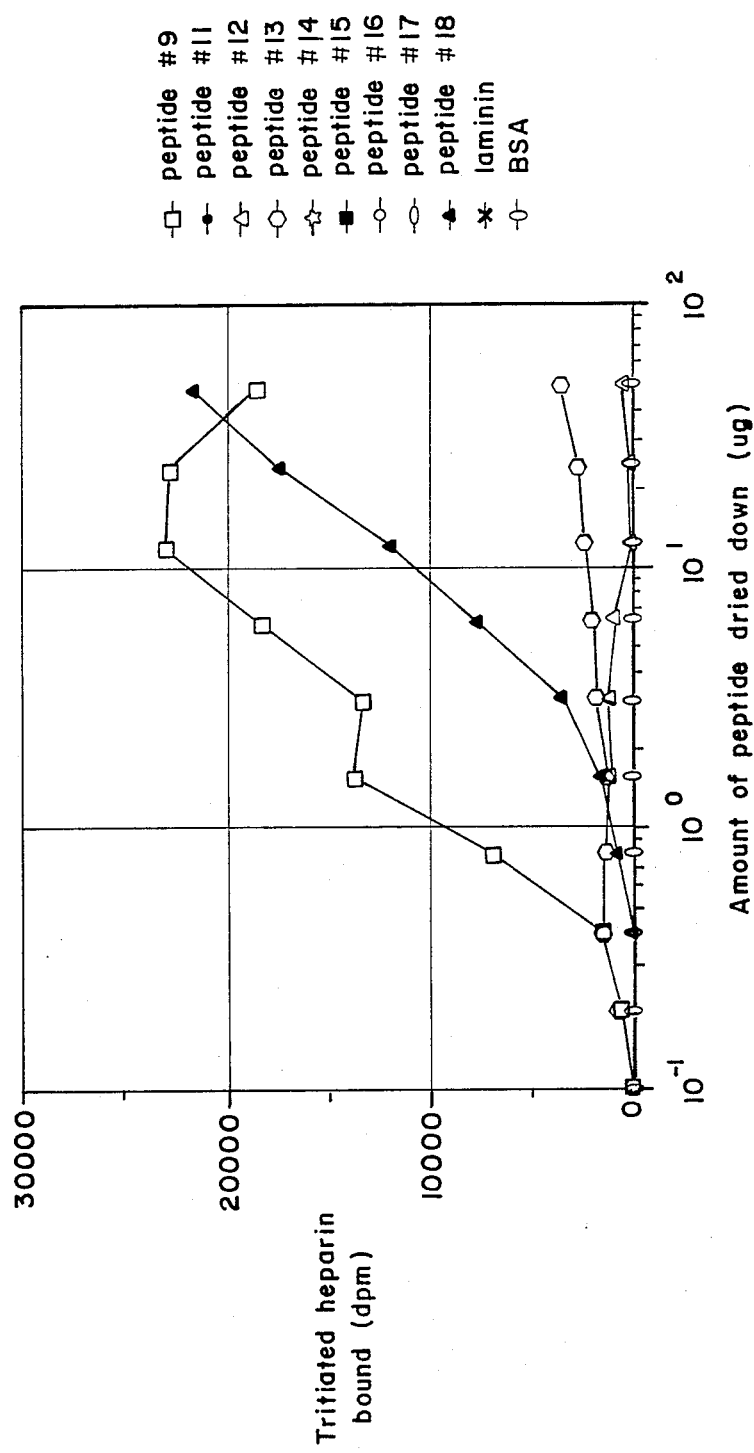
FIG. 5 is a graph depicting heparin binding activity of polypeptide fragments of the invention on plastic plates.

In order to test the ability of the synthesized peptides (9 and 11-18) to bind to 96-well plastic plates (in which experiments with cultured cell lines can be performed), we did an experiment similar to that described above in Example 1. Stock solutions of peptides 9 and 11-18, laminin and BSA at a maximum concentration of 1 mg/ml were prepared and serially diluted in $PBS+NaN_3$ producing final concentration from 1 mg/ml to 1 $\mu$g/ml. Fifty $\mu$l from each concentration was coated on the 96-well plates and left to dry overnight at 28° C. Then, wells were treated for two hours with 200 ml of 2 mg/ml BSA in 6 mM phosphate, 100 mM NaCl, 68 $\mu$M $CaCl_2$, pH 6.8 (wash buffer) in order to minimize non-specific binding. Next 50 $\mu$ls of $^3$H-heparin (10 $\mu$g/ml) was added (50,000 cpm/well) for two hours at 37° C. The wells were then washed three times with wash buffer containing 0.05% Triton X-100 and finally they were incubated for thirty minutes at 60 C with 200 $\mu$l of 0.5 N NaOH and 1% SDS. The amount of $^3$H-heparin bound at each peptide concentration was quantitated as described above in Example 1. The results shown in FIG. 5 indicate that peptide 9 and laminin bind heparin very well and that peptide 13 also binds heparin but less extensively.

EXAMPLE 3. Inhibition of Heparin Binding to Laminin by Peptide Fragments

Figure 6:
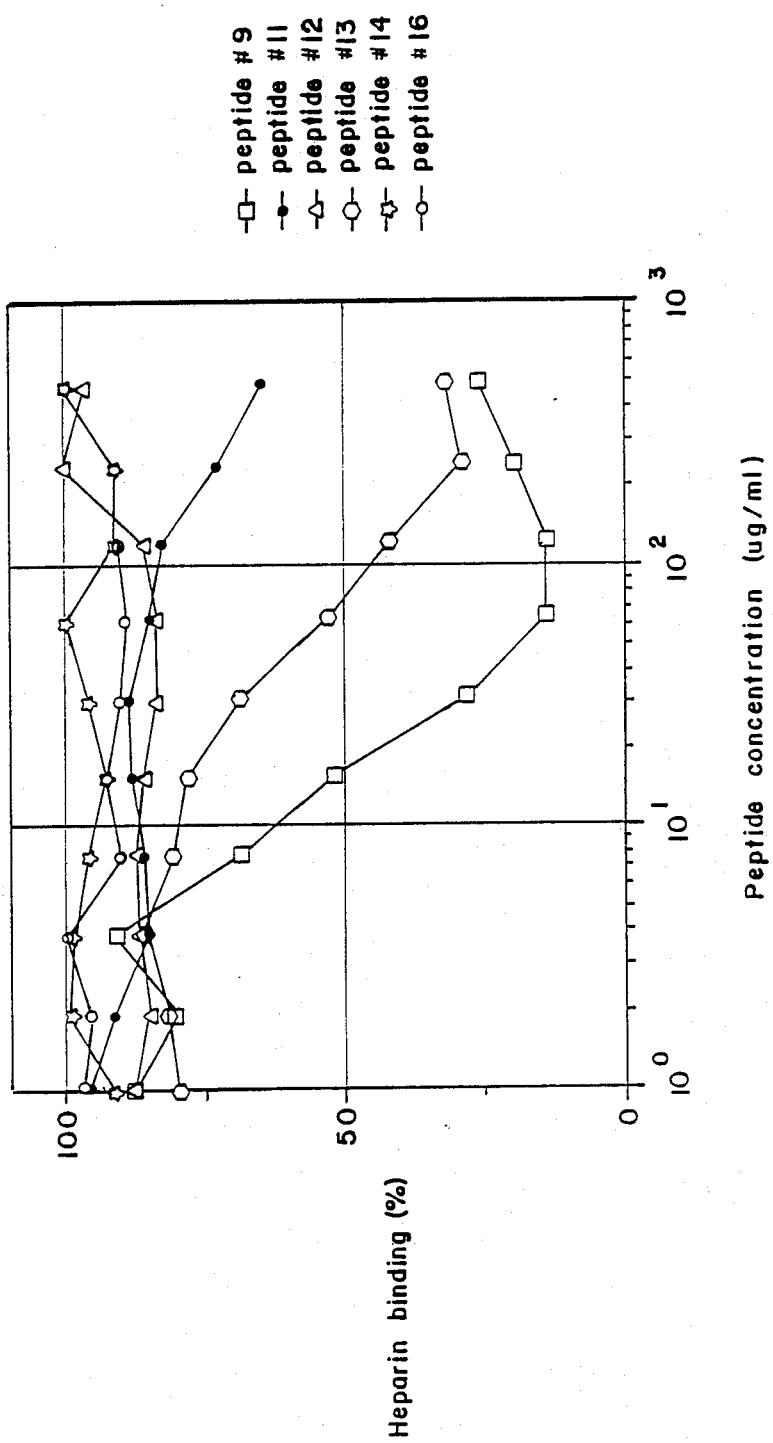
FIG. 6 is a graph depicting inhibition of heparin binding to native laminin by polypeptide fragments of the invention.

Peptides 9, 11-14 and 16 in solution (and not absorbed to plastic), were screened for the ability to inhibit the binding of heparin to intact, native laminin coated on plastic. This experimental approach avoids problems due to differential coating of peptides in heparin binding assays. Laminin at 60 $\mu$g/ml in PBS was coated on 96-well plates, using 50 $\mu$ls per well and dried overnight at 28+ C. The wells were then treated for two hours with 2 mg/ml BSA in wash buffer (described above in Example 2). Peptides at various dilutions ranging from 1 mg/ml to 1 $\mu$g/ml in PBS and CHAPS (Cholamido-propyl-dimethyl-Axmmonio-PropaneSulfonate)(a detergent used to avoid non-specific sticking) were coincubated with a standard amount of $^3$H-heparin (25,000 cpm per well 5 μg/ml final concentration) for two hours at 37° C. and the mixture was then transferred to the laminin coated plate (50 μl) and allowed to incubate for another two hours at 37° C. The wells were then washed and radioactivity was counted as described above. Results shown in FIG. 6 indicate that peptides 9 and 13 interact most strongly with heparin by this assay.

EXAMPLE 4: Heparin/Peptide Interaction Specificity

Figure 7:
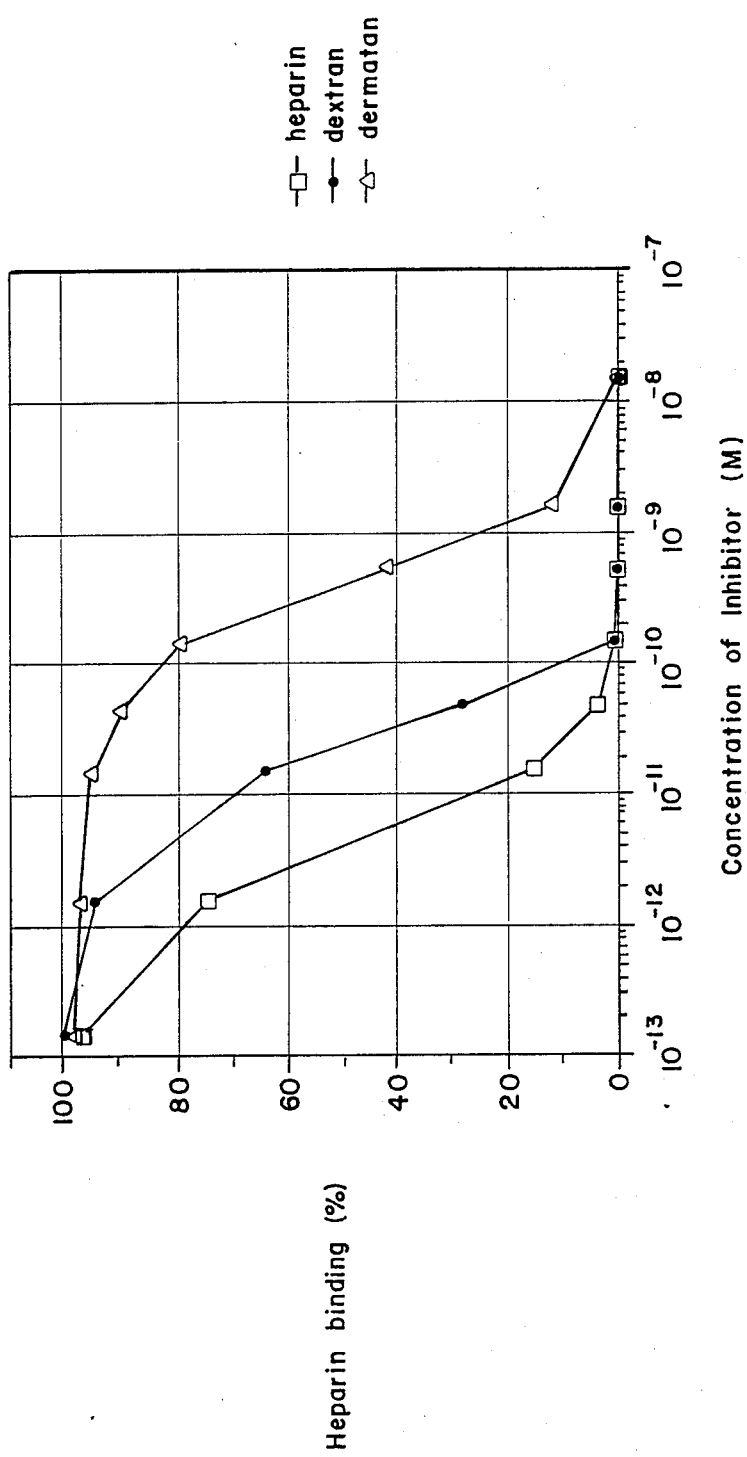
FIGS. 7 and 8 are graphs depicting competition interaction between heparin and other glucosaminoglycans with polypeptides 9 and 13 of the present invention, respectively.
Figure 8:
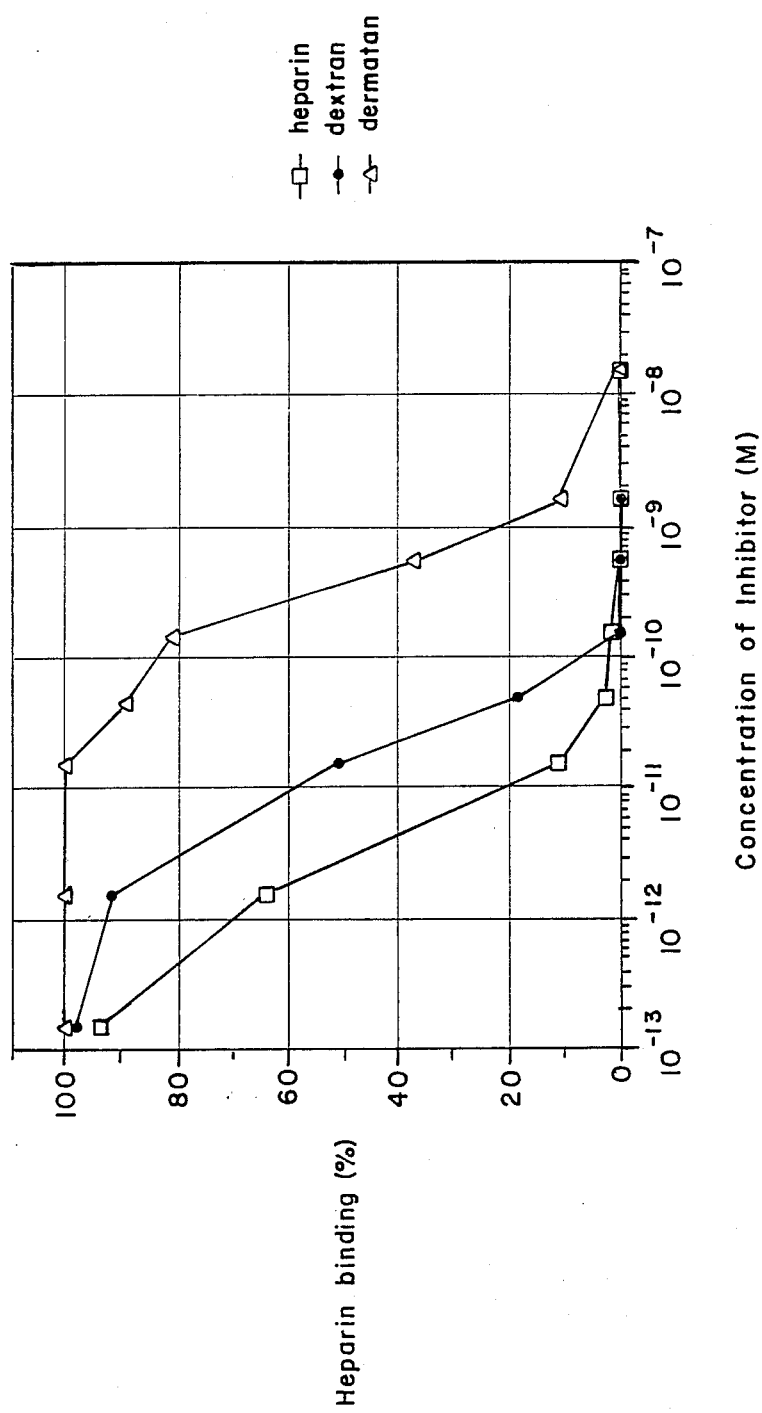

To check whether charge was the main factor in the interaction between heparin and peptides 9 and 13, or whether the heparin structure was also critical to this interaction heparin along with two other sulfated glucosaminoglycans, dextran sulfate and chondroitin sulfate were used in competition experiments. A standard amount of 3.1 μg per well of peptide 9 and 12.5 ug per well of peptide 13 were coated on 96-well plates as described above. We used different concentrations for each peptide in order to monitor the interaction with heparin at a good level of sensitivity, as suggested from the results of Example 2. Wells were treated for two hours with 2 mg/ml BSA in wash buffer. Then, a final volume of 50 μls was added to each well, containing a standard amount of 3H-heparin (50,000 cpm per well) and various amounts of non-radioactive heparin, dextran sulfate and dermatan sulfate. After incubating for two hours at 37° C., the wells were washed and radioactivity was counted as described above in Example 1. As shown in FIG. 7 (for peptide 9) and FIG. 8 (for peptide 13) a 50% inhibition of the binding of $^3$H-heparin can be achieved by $3 \times 10^{-12}$M of heparin. Ten to one hundred times more molar concentration of dextran sulfate and dermatan sulfate are needed to produce the same effect. Therefore, the structure of heparin is a crucial factor for this interaction.

EXAMPLES 1-4 indicated that peptides 9 and 13 are domains on the B1 chain of laminin that can bind specifically with heparin-like molecules.

EXAMPLE 5: Adhesion of Endothelial Cells

A. Isolation of Bovine Aortic Endothelial Cells

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM Na2HP04, pH 7.2) and processed within 2 hours. Crude collagenase (CLS III, 125-145 units per mg dry weight, Cooper Biomedical) was used at 2 mg/ml in Dulbecco's modified Eagle's medium (DMEM) (GIBCO). The vessel was clamped at the distal end, filled with the collagenase-PBS solution and digestion was carried out for 10 minutes. The lumenal contents were harvested, followed by the addition of fresh collagenase for two additional 10-minute periods. The enzyme-cell suspensions were added to an equal volume of DMEM containing 10% fetal bovine serum (FBS) to inhibit the enzyme and spun in a centrifuge at 400×g for 10 minutes. The resulting cell pellet was resuspended in DMEM containing 10% FBS, 100 units/ml of penicillin G, 100 μg/ml of streptomycin and 100 μg/ml of crude fibroblast growth factor. Cells are cultured in 75 cm$^2$ flasks in a humidified 5% CO$_2$ atmosphere at 37° C. Cultures were fed twice a week with the same medium and cells were used in assays when approximately 75% confluent. Cells were identified as endothelial in nature by characteristic cobblestone morphology, contact inhibition of growth upon reaching confluency, and positive immunofluorescent staining for factor VIII:RAg (Miles Laboratories) [S. Schwartz, In Vitro, 14, 966 (1978)]. Only endothelial cells, megakaryocytes and platelets are known to contain the factor VIII:RAg. This method routinely gives a high yield of endothelial cells with little contamination (less than 5%) by smooth muscle cells, pericytes or fibroblasts as judged by phase contrast microscopy as well as by immunostaining.

B. Aortic Endothelial Cell Adhesion Assay

Figure 9:
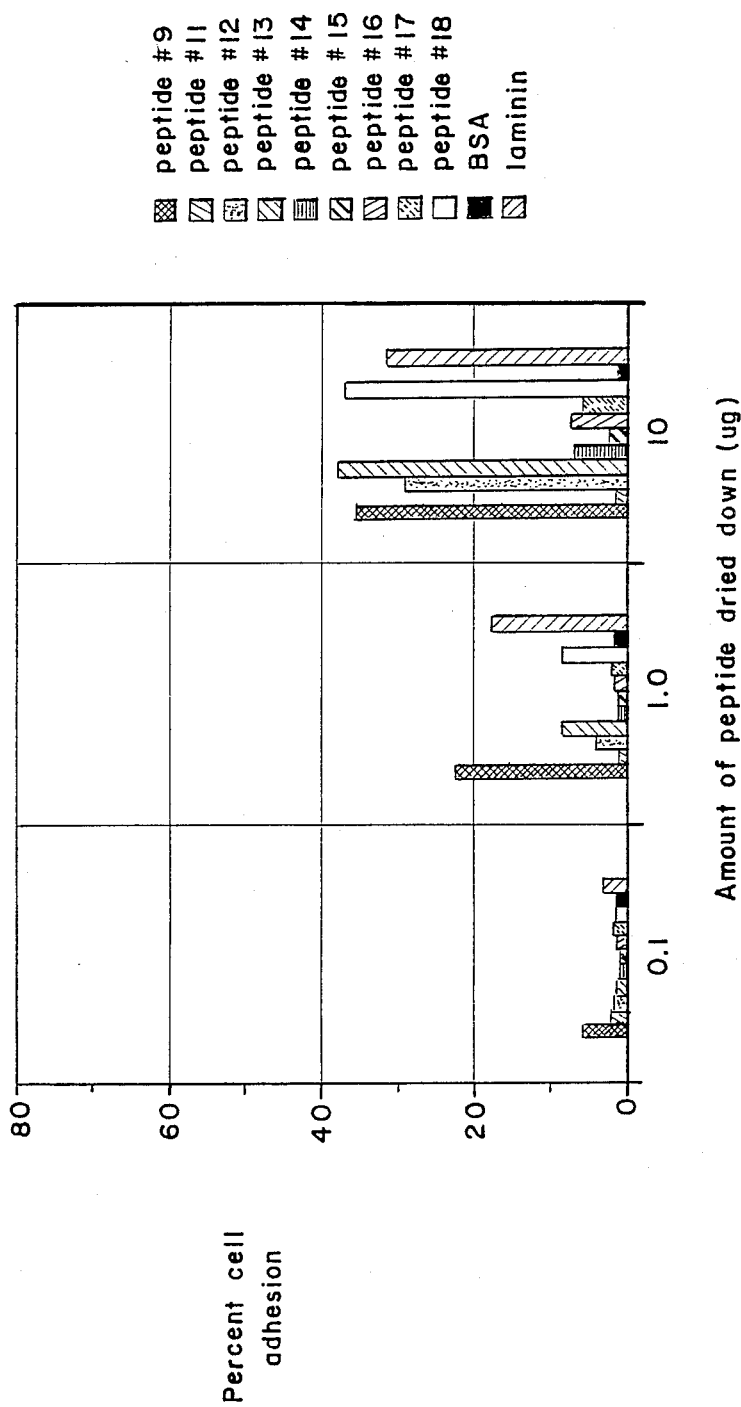

Adhesion was measured using 96 well microtiter plates adsorbed with three different amounts (0.1; 1.0; and 10.0 μg/per well) of peptides 9, 11-18, BSA and laminin. Cultures of cells which were 60-80% confluent were metabolically labeled for 24 hours with the addition of 3 mCi/ml of $^3$H-amino acid mixture. On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4 \times 10^4$/ml and 100 μls of this cell suspension was added to the wells. The assay mixture was then incubated at 37° C for 120 minutes. At the end of the incubation, the wells were washed with warm PBS containing 10 mM Ca$^{++}$, and the adherent population was solubilized with 0.5N NaOH containing 1% sodium dodecyl sulfate. The solubilized cells were then quantitated using a liquid scintillation counter. Each determination was done in triplicate. The results of this study are summarized in FIG. 9 below.

These results indicate that peptides 9 and 13 and 12 and 18 are potent promoters of endothelial cell adhesion. Thus, these peptides may be useful as a synthetic substratum to promote endothelial cell adhesion.

Example 6. Adhesion of Cancer Cells

A. Isolation of and Cell Adhesion for M4 cell line

Highly metastatic murine melanoma cells, K-1735-M4 were originally provided by Dr. I. J. Fidler of Anderson Hospital, University of Texas Health Sciences Center, Houston, Tex. When the cells were received, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments. This precaution is taken to minimize phenotypic drift that can occur as a result of continuous in vitro passage. The cells were cultured in Dulbecco's Modified Eagle's Medium containing 5% heat inactivated fetal calf serum. The cultures were grown in 37° C. incubators with a humidified atmosphere containing 5% CO$_{02}$. Cells were subcultured twice weekly by releasing cells gently from the flask, using 0.05% trypsin and 1 mM EDTA.

Figure 10:
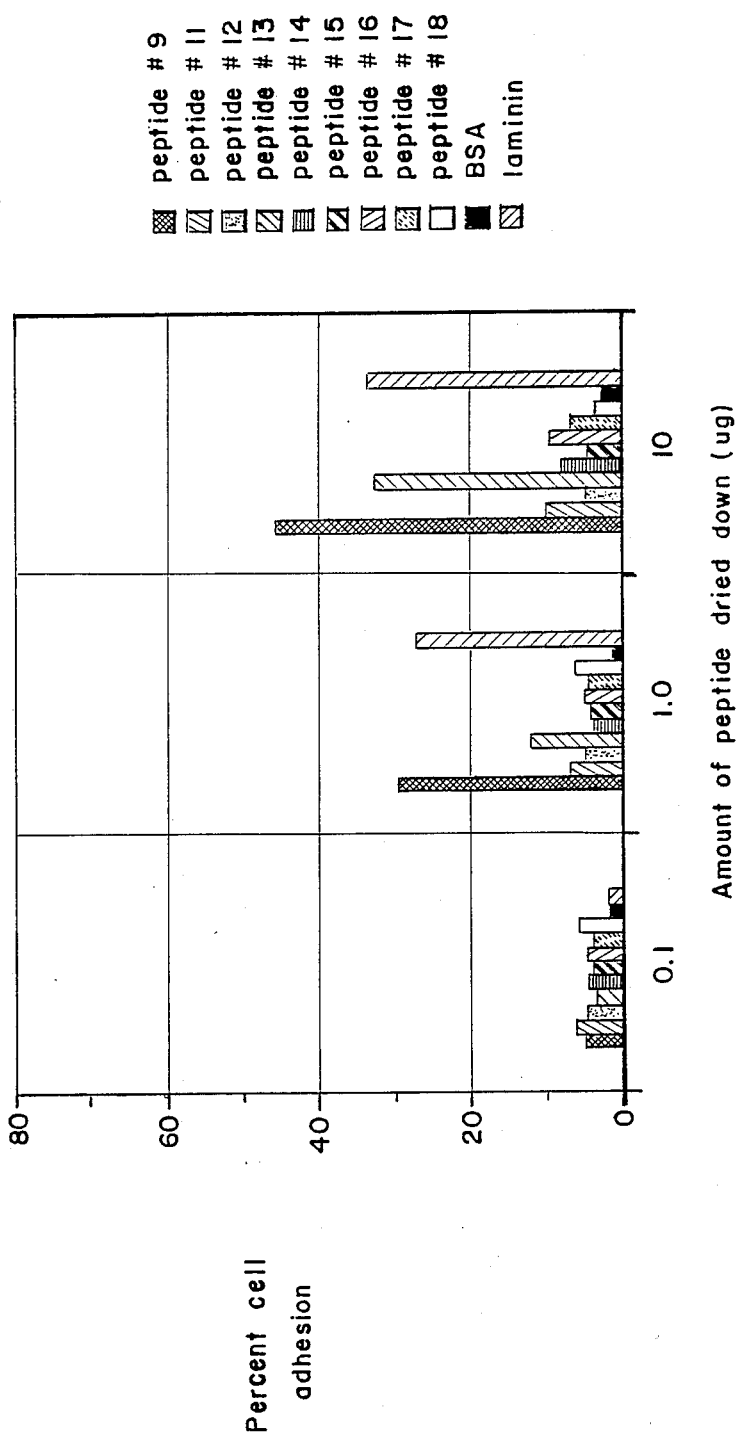

The melanoma cells were pulsed in the same fashion as the endothelial cells described hereinabove, except that 3 mCi/ml $^3$HTd(tritiated thymidine) was added to each culture instead of amino acids. The labeled cells were harvested as described for the endothelial cells. The cell adhesion assay was identical to that described hereinabove for the bovine aortic endothelial cell assay. The results of this assay are summarized in FIG. 10, below.

B. Isolation of and Cell Adhesion Assay for MM fibrosarcoma Cell Line

Figure 11:
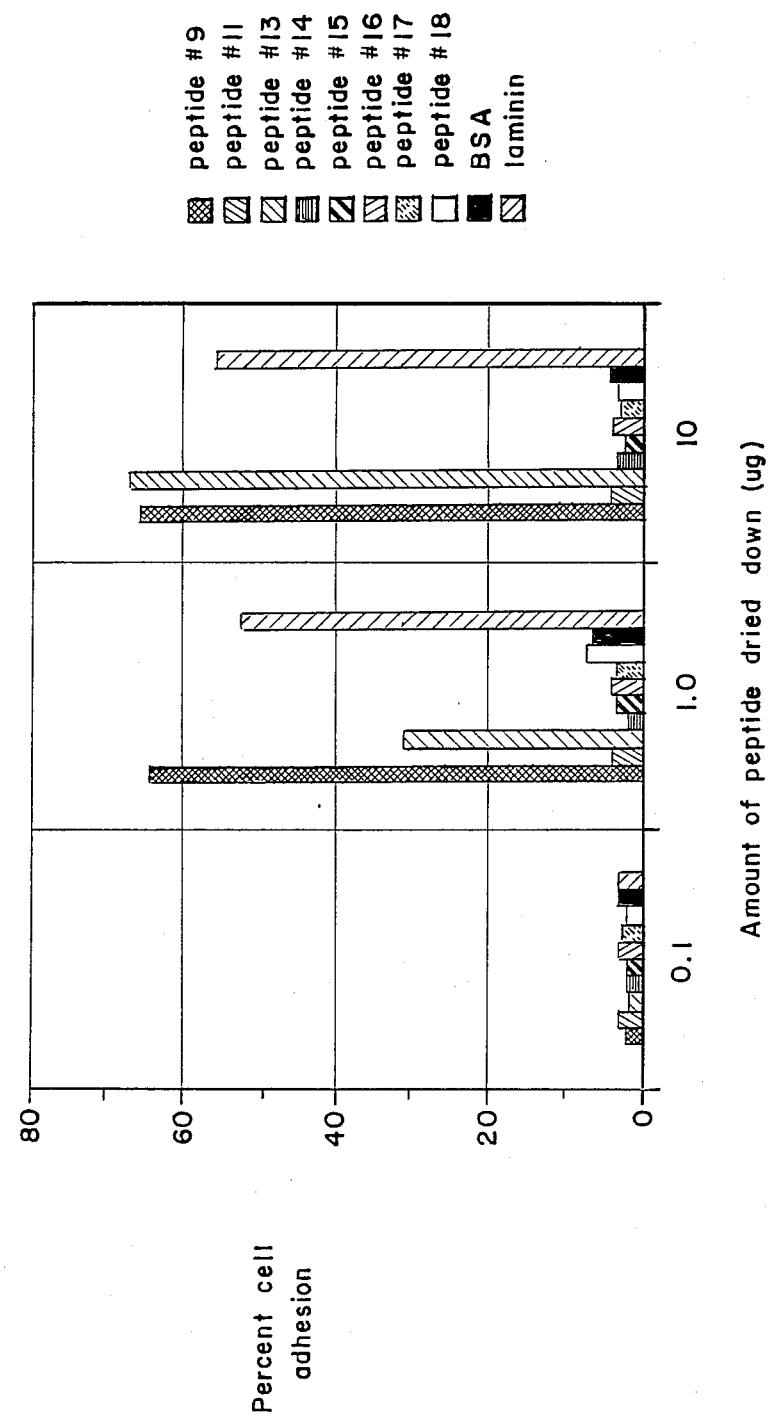

Murine fibrosarcoma cells (uv-2237-MM) were originally provided by Dr. I. J. Fidler of Anderson Hospital, University of Texas Health Sciences Center, Houston, Tex. Culturing, labeling and harvesting techniques were as described in part A. Cell adhesion assay was performed as described in Example 5. The results of this assay are summarized in FIG. 11 below.

C. Isolation of and Cell Adhesion Assay for C6 Cell Line

Figure 12:
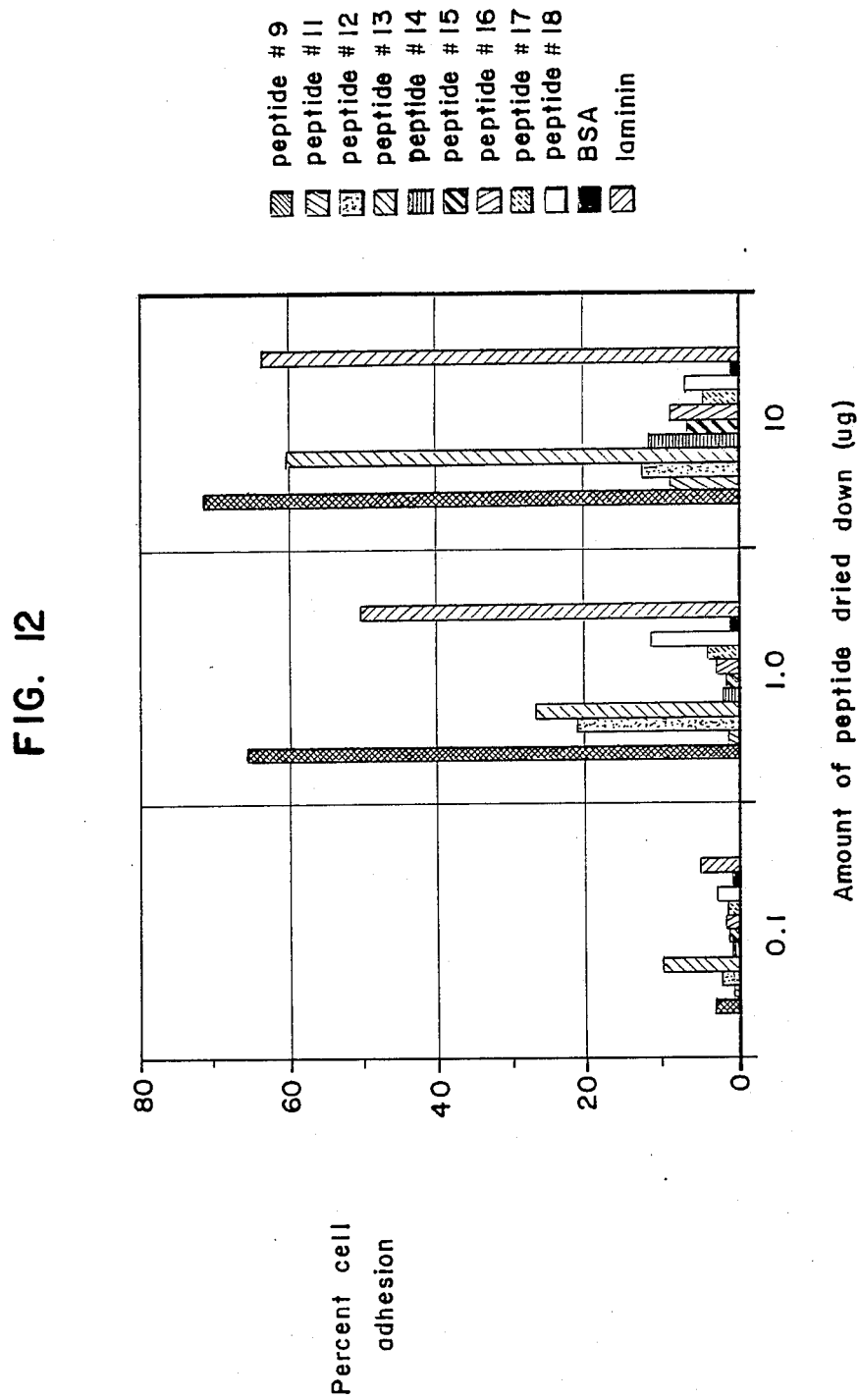

Rat C6 glioma cell line was purchased from the American Type Culture Collection (identification number CCL 107). Culturing techniques were as described in part A. Labelling and harvesting techniques were as described in Example 5. Cell adhesion assay was performed as described in Example 5. The results of this assay are summarized in FIG. 12 below.

D. Isolation of and Cell Adhesion Assay for PC12 Pheochromocytoma Cell Line

PC12 rat pheochromocytoma cells were provided by Dr. P. Letourneau of the Department of Anatomy, University of Minnesota, Minneapolis, Minn. Culturing techniques were as described in part A. Labelling and harvesting techniques were as described in Example 5. Cell adhesion assay was performed as described in Example 5. The results of this assay are summarized in FIG. 13 below.

EXAMPLES 5 and 6A-D indicate that peptides 9 and 13 are potent promoters of cell adhesion for a wide range of cell lines.

A number of practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron TM (polyethylene terephthalate) fiber. Most types of cells are attracted to laminin and to the present polypeptides. Endothelial cells and fibroblastic cells are especially attracted to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumae, e.g., spinal cord injuries.

In such cases, it may be advantageous to couple the peptide to a biological molecule, such as collagen, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, the polypeptides of the present invention can be used to promote cell adhesion of various cell types to naturally occurring or artificial substrata intended for use in vitro. For example, a culture substrate such as the wells of a microtiter plate or the medium contacting surface of microporous fibers or beads, can be coated with the cell-attachment polypeptides. This can obviate the use of laminin in the medium, thus providing better defined conditions for the culture as well as better reproducibility.

As one example of commercial use of cellattachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of coating protein in the growth medium and the present polypeptides are expected to provide an improved, chemically-defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines (McCarthy et al, supra). This effect is mediated via the saturation and therefore neutralization of cell surface receptors for laminin. In accordance with the present invention, the data presented herein suggest that receptors for the polypeptides 9 and 13 should exist on cell surfaces of malignant cells. Consequently, these polypeptides could be used to block laminin receptors of metastatic cells and therefore reduce their metastatic potential.

The invention has been described with reference to various specific and preferred embodiments and techniques. However, it should be understood that many variations and modifications may be made while remaining within the spirit and scope of the invention.

What is claimed is:

1. A polypeptide of the formula:

arg-tyr-val-val-val-leu-pro-arg-pro-val-cys-phe-glu-lys-gly-met-asn-tyr-thr-val-arg, or glu-leu-thr-asn-arg-thr-his-lys-phe-leu-glu-lys-ala-lys-ala-leu-lys ile or mixtures thereof.

2. A polyypepetide of the formula:
arg-tyr-val-val-val-leu-pro-arg-pro-val-cys-phe-glu-lys-gly-met-asn-tyr-thr-val-arg.

3. A polypeptide of the formula:

glu-leu-thr-asn-arg-thr his-lys-phe-leu-glu-lys-ala-lys-ala-leu-lys-ile.

* * * * *

UNITED STATES PATENT AND TRADEMARK OFFICE
CERTIFICATE OF CORRECTION

PATENT NO. : 4,870,160

DATED : September 26, 1989

INVENTOR(S) : Aristidis S. Charonis et al.

It is certified that error appears in the above-identified patent and that said Letters Patent is hereby corrected as shown below:

On page 1, in the Abstract, line 4 after "val-" (1st) insert --val- --.

On page 1, in the Abstract, line 8 for "medical" read --Medical--.

In column 1, line 58 delete "i" after --al.,--.

In column 1, line 64 for "selfassociate" read --self-associate--.

In column 6, line 63 for "28+" read --28°--.

In column 6, line 67 for "Axmmonio" read --Ammonio--.

In column 6, line 67 for "PropaneSulfonate" read --Propane-Sulfonate--.

In column 7, line 24 for "3H-heparin" read --$^3$H-heparin--.

In column 7, line 31 for "$10^{--12}M$" read --$10^{-12}M$--.

In column 8, line 57 for "$CO_{02}$" read --$CO_2$--.

In column 9, lines 52-53 for "Dacron$^{TM}$" read --DACRON$^{TM}$--.

In column 10, line 20 for "cellattachment" read --cell-attachment--.

UNITED STATES PATENT AND TRADEMARK OFFICE
CERTIFICATE OF CORRECTION

PATENT NO. : 4,870,160

DATED : September 26, 1989

INVENTOR(S) : Aristidis S. Charonis et al.

It is certified that error appears in the above-identified patent and that said Letters Patent is hereby corrected as shown below:

In column 10, in claim 1, line 2 delete "val-" after --tyr--.

In column 10, in claim 1, line 5 for "lys ile" read --lys-ile--.

Signed and Sealed this

Ninth Day of February, 1993

Attest:

STEPHEN G. KUNIN

Attesting Officer

Acting Commissioner of Patents and Trademarks